(12) United States Patent
Sherman

(10) Patent No.: US 7,074,429 B2
(45) Date of Patent: Jul. 11, 2006

(54) FOSINOPRIL SODIUM TABLET FORMULATION

(76) Inventor: Bernard Charles Sherman, 50 Old Colony Road, Willowdale, Ontario (CA) M2L 2K1

(*) Notice: Subject to any disclaimer, the term of this patent is extended or adjusted under 35 U.S.C. 154(b) by 0 days.

(21) Appl. No.: 10/042,352

(22) Filed: Jan. 11, 2002

(65) Prior Publication Data

US 2002/0131999 A1 Sep. 19, 2002

(30) Foreign Application Priority Data

Jan. 11, 2001 (CA) .................................... 2330904

(51) Int. Cl.
*A61K 9/20* (2006.01)
(52) U.S. Cl. .................. 424/465; 424/401; 424/464
(58) Field of Classification Search ................ 424/405, 424/408, 464, 465, 401
See application file for complete search history.

(56) References Cited

U.S. PATENT DOCUMENTS

| | | | | |
|---|---|---|---|---|
| 4,189,492 A | * | 2/1980 | Sjoerdsma | .................. 424/273 |
| 4,337,201 A | | 6/1982 | Petrillo, Jr. | |
| 5,006,344 A | * | 4/1991 | Jerzewski et al. | .......... 424/465 |
| 5,095,110 A | * | 3/1992 | Flynn et al. | ................ 540/522 |
| 5,225,401 A | * | 7/1993 | Seymour | ..................... 514/19 |
| 5,492,904 A | * | 2/1996 | Wong | ......................... 514/211 |

* cited by examiner

*Primary Examiner*—Michael G. Hartley
*Assistant Examiner*—Micah-Paul Young
(74) *Attorney, Agent, or Firm*—Neil H. Hughes; Ivor M. Hughes; Marcelo Sarkis

(57) ABSTRACT

Stable tablets comprising fosinopril sodium are prepared by employing either stearic acid or zinc stearate as the lubricant.

11 Claims, No Drawings

FOSINOPRIL SODIUM TABLET FORMULATION

BACKGROUND OF THE INVENTION

Fosinopril sodium is a medicinal compound useful as an antihypertensive agent. Its ability to inhibit the angiotension converting enzyme and thus lower blood pressure is disclosed in U.S. Pat. No. 4,337,201.

U.S. Pat. No. 5,006,344 explains that tablets comprising fosinopril sodium are relatively unstable when the tablets also comprise magnesium stearate as the lubricant. This patent further discloses that tablets with improved stability can be obtained by eliminating magnesium stearate and instead using as the lubricant either sodium stearyl fumarate or hydrogenated vegetable oil.

Sodium stearyl fumarate is said to be preferred since hydrogenated vegetable oil can cause processing problems of sticking to the punch tips (i.e. inadequate lubrication) during long tabletting runs.

Tablets comprising fosinopril sodium are now sold in the United States under the tradename Monopril™. These tablets are made in accordance with the teaching of U.S. Pat. No. 5,006,344 and comprise sodium stearyl fumarate as the lubricant.

While sodium stearyl fumarate appears to be an effective lubricant for fosinopril sodium tablets, it is much more expensive than other lubricants and is not commonly used.

The object of the present invention is thus to find a lubricant for fosinopril sodium tablets other than sodium stearyl fumarate, that is effective as a lubricant, and that is relatively inexpensive.

SUMMARY OF THE INVENTION

It has been found that both stearic acid and zinc stearate are effective lubricants for fosinopril sodium tablets.

Moreover, it has been surprisingly found that, unlike magnesium stearate and calcium stearate, neither stearic acid nor zinc stearate causes the tablets to be unstable.

The invention is thus a pharmaceutical tablet comprising fosinopril sodium along with either stearic acid or zinc stearate as the lubricant.

DETAILED DESCRIPTION OF THE INVENTION

In addition to fosinopril sodium as the active ingredient, and either stearic acid or zinc stearate as the lubricant, the tablet formulation will also comprise at least one other excipient as a filler and binder, such as, for example, lactose or microcrystalline cellulose. The preferred filler is lactose.

The tablet will also optionally comprise a disintegrant, such as, for example, starch, croscarmellose sodium, sodium starch glycolate, or crospovidone. The tablet will also optionally comprise other excipients, such as a colour agent. The tablet will also optionally contain another active ingredient, such as a diuretic.

The quantity of the lubricant as a percentage of the total tablet weight will preferably be from about 0.3 percent to about 4.0 percent.

The fosinopril sodium tablets of this invention can be prepared by conventional tablet forming techniques such as, for example, wet granulation and dry granulation. In the wet granulation process, the active ingredient or ingredients are mixed with some or all of the filler. This blend is then wet granulated with a solution of a binder in solvent. The resultant wet granulation is then dried and milled. The granules are then mixed with the remaining ingredients, which will include the lubricant, to produce the final mix, which is then compressed into tablets.

In the dry granulation process, the active ingredient or ingredients are mixed with the other ingredients without addition of any solvent, and thus without the need for drying. Again the final mix is compressed into tablets. The dry granulation approach is preferred as it is simpler and thus less costly.

The invention will be further understood from the following examples:

|  | Example No: | | | | |
| --- | --- | --- | --- | --- | --- |
|  | 1 | 2 | 3 | 4 | 5 |
| Fosinopril Sodium | 10.0 | 10.0 | 10.0 | 10.0 | 10.0 |
| Lactose Anhydrous | 188.0 | 188.0 | 188.0 | 186.0 | 188.0 |
| Magnesium Stearate | 2.0 | X | X | X | X |
| Zinc Stearate | X | 2.0 | X | X | X |
| Calcium Stearate | X | X | 2.0 | X | X |
| Stearic Acid | X | X | X | 4.0 | X |
| Sodium Stearyl Fumarate | X | X | X | X | 2.0 |
|  | 100.0 | 100.0 | 100.0 | 100.0 | 100.0 |

For each of the 5 examples, the ingredients in the proportions listed were mixed together. The powder mixture was then passed through a #40 screen and mixed again. The powder mixture was then compressed into tablets of weight 100 mg each, so that each tablet contained 10 mg of fosinopril sodium.

Tablets of each of the examples were stored at 60° C. for two weeks and then tested by an HPLC method to determine the degradation products as a percentage of the initial fosinopril sodium content.

The results were as follows:

| Example No. | Lubricant | % Degradation Products |
| --- | --- | --- |
| 1 | Magnesium Stearate | 46.2% |
| 2 | Zinc Stearate | 1.7% |
| 3 | Calcium Stearate | 75.5% |
| 4 | Stearic Acid | 2.1% |
| 5 | Sodium Stearyl Fumarate | 2.8% |

For example 1, using magnesium stearate, the degradation products total 46.2%, whereas for example 5, using sodium stearyl fumarate, the degradation products total only 2.8%. This confirms the teaching of U.S. Pat. No. 5,006,344 that stability is very much improved by using sodium stearyl fumarate as lubricant instead of magnesium stearate.

Example 3, using calcium stearate, shows degradation products totalling 75.5%, which is even worse than obtained using magnesium stearate.

However, example 2, using zinc stearate, shows degradation products totalling only 1.7% and example 4, using stearic acid, shows degradation products totalling only 2.1%.

It is thus found that, while degradation rate is high when either magnesium stearate or calcium stearate is used as lubricant, the degradation rate is low when either zinc stearate or stearic acid is used as lubricant.

The invention claimed is:

1. A pharmaceutical tablet comprising fosinopril sodium and zinc stearate as lubricant, wherein the rate of degradation of fosinopril sodium is reduced relative to the same fosinopril sodium tablet but comprising as lubricant magnesium stearate, or calcium stearate, instead of zinc stearate as lubricant.

2. The tablet of claim 1 further comprising lactose.

3. The tablet of claim 1 wherein the amount of zinc stearate by weight is from about 0.3 percent to about 4.0 percent of the total tablet weight.

4. The tablet of claim 2 wherein the amount of zinc stearate by weight is from about 0.3 percent to about 4.0 percent of the total tablet weight.

5. A pharmaceutical tablet comprising fosinopril sodium and zinc stearate as lubricant in an amount by weight from about 0.3% to about 4.0% of the total weight, wherein the rate of degradation of fosinopril sodium is reduced relative to the same fosinopril sodium tablet but comprising as lubricant magnesium stearate or calcium stearate instead of zinc stearate as lubricant.

6. The tablet of claim 5 further comprising at least one excipient selected from lactose, microcrystalline cellulose, starch, crosscarmellose sodium, sodium starch glycolate, crospovidone, or colouring.

7. A method of reducing degradation of fosinopril sodium when it is formulated into a dosage form with a lubricant, the method comprising formulating fosinopril sodium using zinc stearate as lubricant.

8. A pharmaceutical tablet comprising fosinopril sodium and zinc stearate as lubricant, wherein the degradation of fosinopril sodium in the tablet is reduced relative to the same fosinopril sodium tablet but comprising, magnesium stearate, or calcium stearate as lubricant instead of zinc stearate as lubricant.

9. The tablet of claim 8 further comprising lactose.

10. The tablet of claim 8 or 9 wherein the amount of zinc stearate by weight is from about 0.3% to about 4.0% of the total tablet weight.

11. The tablet of claim 10 further comprising at least one excipient selected from lactose, microcrystalline cellulose, starch, crosscarmellose sodium, sodium starch glycolate, crospovidone, or colouring.

* * * * *